United States Patent
Li et al.

(10) Patent No.: US 9,007,869 B2
(45) Date of Patent: Apr. 14, 2015

(54) ULTRASOUND IMAGING SYSTEM

(71) Applicant: National Taiwan University, Taipei (TW)

(72) Inventors: Pai-Chi Li, Taipei (TW); Yen-Feng Li, Taipei (TW)

(73) Assignee: National Taiwan University, Taipei (TW)

(*) Notice: Subject to any disclaimer, the term of this patent is extended or adjusted under 35 U.S.C. 154(b) by 123 days.

(21) Appl. No.: 13/746,548

(22) Filed: Jan. 22, 2013

(65) Prior Publication Data

US 2014/0126323 A1    May 8, 2014

(30) Foreign Application Priority Data

Nov. 7, 2012 (TW) .............................. 101141329 A

(51) Int. Cl.
G03B 42/06 (2006.01)
A61B 8/08 (2006.01)
G01S 15/89 (2006.01)

(52) U.S. Cl.
CPC ............... *A61B 8/08* (2013.01); *G01S 15/8981* (2013.01); *G01S 15/8927* (2013.01)

(58) Field of Classification Search
CPC ........ G03B 42/06; A61B 8/00; A61B 8/5207; A61B 8/565
USPC ...................................... 367/7, 11
See application file for complete search history.

(56) References Cited

U.S. PATENT DOCUMENTS

| | | | |
|---|---|---|---|
| 5,555,534 A * | 9/1996 | Maslak et al. ..................... 367/7 |
| 2005/0131299 A1* | 6/2005 | Robinson et al. ............. 600/447 |
| 2007/0167752 A1* | 7/2007 | Proulx et al. .................. 600/437 |
| 2012/0157846 A1* | 6/2012 | Li et al. .......................... 600/443 |
| 2013/0211252 A1* | 8/2013 | LI et al. ......................... 600/437 |
| 2014/0126323 A1* | 5/2014 | LI et al. ........................... 367/7 |

FOREIGN PATENT DOCUMENTS

CN          102551794 A *  7/2012

* cited by examiner

*Primary Examiner* — Daniel Pihulic
(74) *Attorney, Agent, or Firm* — Rosenberg, Klein & Lee

(57) ABSTRACT

An ultrasonic imaging system for generating an ultrasonic image of a motion status of an object according to at least an ultrasonic motion signal generated by detecting the motion of the object is provided. The ultrasonic imaging system includes a demodulation module, an analog sub-array beamformer, a filter, an analog-to-digital converter and an image processing module. The demodulation module receives and demodulates the ultrasonic motion signal so as to generate and send at least a demodulated signal. The analog sub-array beamformer receives the demodulated signal, generates and sends an analog sub-array beam signal according to the demodulated signal. The filter receives and filtering the analog sub-array beam signal. The analog-to-digital converter converts the analog sub-array beam signal filtered by the filter into a digital sub-array beam signal. The image processing module receives the digital sub-array beam signal so as to generate an ultrasonic image of the motion of the object.

10 Claims, 2 Drawing Sheets

ULTRASOUND IMAGING SYSTEM

This application claims the benefits of the Taiwan Patent Application Serial NO. 101141329 filed on Nov. 7, 2012, the subject matter of which is incorporated herein by reference.

BACKGROUND OF THE INVENTION

1. Field of the Invention

The present invention relates to an ultrasonic imaging system and more particularly, relates to an imaging system including a single filter module filtering an analog sub-array beam signal and performing digital beamforming.

2. Description

The technique of generating images by means of ultrasound has been widely applied to people's life due to the development of science and technology. Compared with medical imaging systems such as X-ray, CT, MRI and nuclear medicine imaging utilized in clinic, ultrasonic imaging has advantages of competitive price, non-invasiveness, radiation free, instant imaging, spatial resolution of centimeters in images, portability, flow estimation ability, etc. Thus, ultrasonic imaging is commonly applied to clinical diagnosis in every medical category.

The principle of ultrasonic imaging is to reconstruct an image of an object to be detected with the characteristics of diffraction and reflection of sound waves. When ultrasonic imaging is utilized in flow velocity estimation, since signals of flow velocity are weaker, signals of a motionless object need to be filtered via a filter in order to obtain a precise result of flow velocity estimation. However, traditionally a clutter filtering is performed on signal via analog or digital method, i.e. analog clutter filter or digital clutter filter. With digital clutter filtering, signal distortion may occur due to quantization error and a large amount of digital hardware resource is required for data storage and signal processing; with analog clutter filtering, beamforming is forced to be done via analog method so that advantages of programmability and precision of digital beamforming are missed.

Besides, a multiple-gated flow velocity estimation is required when users hope not to lose range images of the flow velocity estimation. However, since signals sent and received have to be temporarily stored for the multiple-gated flow velocity estimation and since Doppler gates with the same range have to be found for the calculation of flow velocity, several clutter filters are required for calculating simultaneously in different range of the Doppler gates in order to speed up imaging. As a result, costs on scratchpad memory and computing of hardware are considerable.

SUMMARY OF THE INVENTION

In prior art, a digital clutter filtering requires a large amount of resources of digital hardware for data storage and signal processing; an analog clutter filtering does not have advantages of programmability and precision as digital beamforming does. Moreover, if users hope not to lose range images of the flow velocity estimation, a multiple-gated flow velocity estimation is required, which causes problems of considerable costs on scratchpad memory and computing of hardware.

Thus, an ultrasonic imaging system is provided according to an embodiment of present invention, wherein an analog sub-array beam signal is filtered with a clutter filter and is performed with beamforming. Besides, an ultrasonic imaging system is provided according to an embodiment of present invention, the system including a single filter module for multiple-gated clutter filtering and timely data output.

An ultrasonic imaging system is provided for generating an ultrasonic image of a motion status of an object according to at least an ultrasonic motion signal generated by detecting a motion of the object, the system including at least a demodulation module, at least an analog sub-array beamformer, at least a filter, at least an analog-to-digital converting module and an image processing module. The demodulation module receives and demodulates the ultrasonic motion signal to generate and send at least a demodulated signal; the analog sub-array beamformer electrically connects the demodulation module, receives the demodulated signal, generates and sends an analog sub-array beam signal according to the demodulated signal.

The filter electrically connects the analog sub-array beamformer, receives and filters the analog sub-array beam signal. The analog-to-digital converting module electrically connects the filter and converts the analog sub-array beam signal filtered by the filter into a digital sub-array beam signal. The image processing module receives the digital sub-array beam signal to generate an ultrasonic image of the motion of the object.

Preferably, the system further includes at least an ultrasonic probe electrically connecting the demodulation module, the ultrasonic probe detecting the motion of the object and generating the ultrasonic motion signal. Besides, the analog sub-array beamformer includes at least a phase retarder and an adder, the phase retarder electrically connecting the demodulation module, and adder electrically connecting the phase retarder, the phase retarder delaying the phase of the demodulated signal, the adder summing the phase delayed demodulated signal and generating the analog sub-array beam signal accordingly.

According to an embodiment of the present invention, the system further includes an integrator disposed between the analog sub-array beamformer and the filter, the integrator electrically connecting the analog sub-array beamformer and the filter to perform integration of the analog sub-array beam signal. Moreover, the image processing module includes a differentiator to differentiate the digital sub-array beam signal; the image processing module further includes a digital beamforming unit and a motion detecting unit, the motion detecting unit electrically connecting the digital beamforming unit, the digital beamforming unit forming at least a digital beam and generating the ultrasonic image according to the digital sub-array beam signal, the motion detecting unit detecting the motion status of the object according to the ultrasonic image.

According to an embodiment of the present invention, the system further includes an amplifier disposed between the filter and the analog-to-digital converting module, the amplifier electrically connecting the filter and the analog-to-digital converting module to amplify the analog sub-array beam signal filtered by the filter. Besides, the image processing module is coupled to the analog-to-digital converting module and goes through at least a processing selected from the group of an image synthesis, an image analysis, an image calculation, an image data storage and a diagnosis assistance; the filter is selected from the group of a high pass filter, a band pass filter and a low pass filter.

Compared with prior art, since the ultrasonic imaging system provided according to embodiments of the present invention performs analog clutter filtering and digital beamforming, it is characterized with high sensitivity and low power of analog clutter filtering and also with programmability and precision of digital beamforming; thus, a large amount of digital hardware resource for data storage and signal processing is not required and advantages of programmability and precision of digital are not missed.

Besides, according to an embodiment of the present invention, since merely one single filter module is needed for each sub-array to perform multiple-gated clutter filtering and timely data output, and not to lose range images, users does not need to wait for each Doppler gate to calculate so as to filter. Thus, it is not needed for embodiments of present invention to temporarily store the signals and thus the costs on scratchpad memory and computing of hardware are saved. (The single filter module includes an analog sub-array beamformer electrically connecting a filter; in prior art, an analog sub-array beamformer needs to be electrically connected to multiple filters in order to perform multiple-gated calculation.)

BRIEF DESCRIPTION OF THE DRAWINGS

Other features and advantages of this invention will become more apparent in the following detailed description of the preferred embodiments of this invention, with reference to the accompanying drawings, in which.

DETAILED DESCRIPTION OF THE PREFERRED EMBODIMENT

The present invention relates to an ultrasonic imaging system. In the following description, numerous details are set forth in order to provide a thorough understanding of the present invention. It will be appreciated by one skilled in the art that variations of these specific details are possible while still achieving the results of the present invention. In other instance, well-known components are not described in detail in order not to unnecessarily obscure the present invention.

Figure 1:
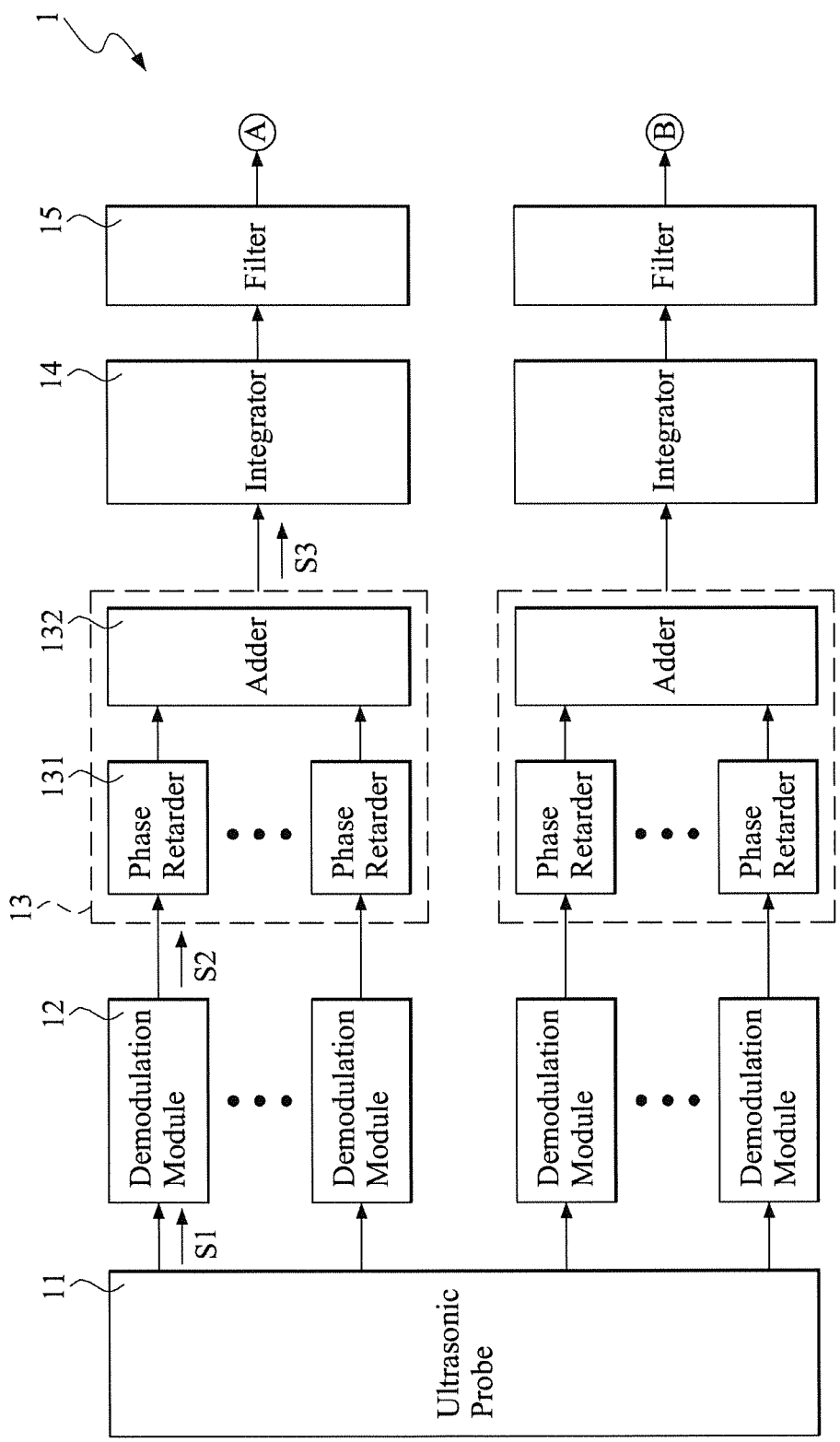
FIG. 1 and FIG. 1A are schematic views showing an ultrasonic imaging system according to an embodiment of the present invention.
Figure 1A:
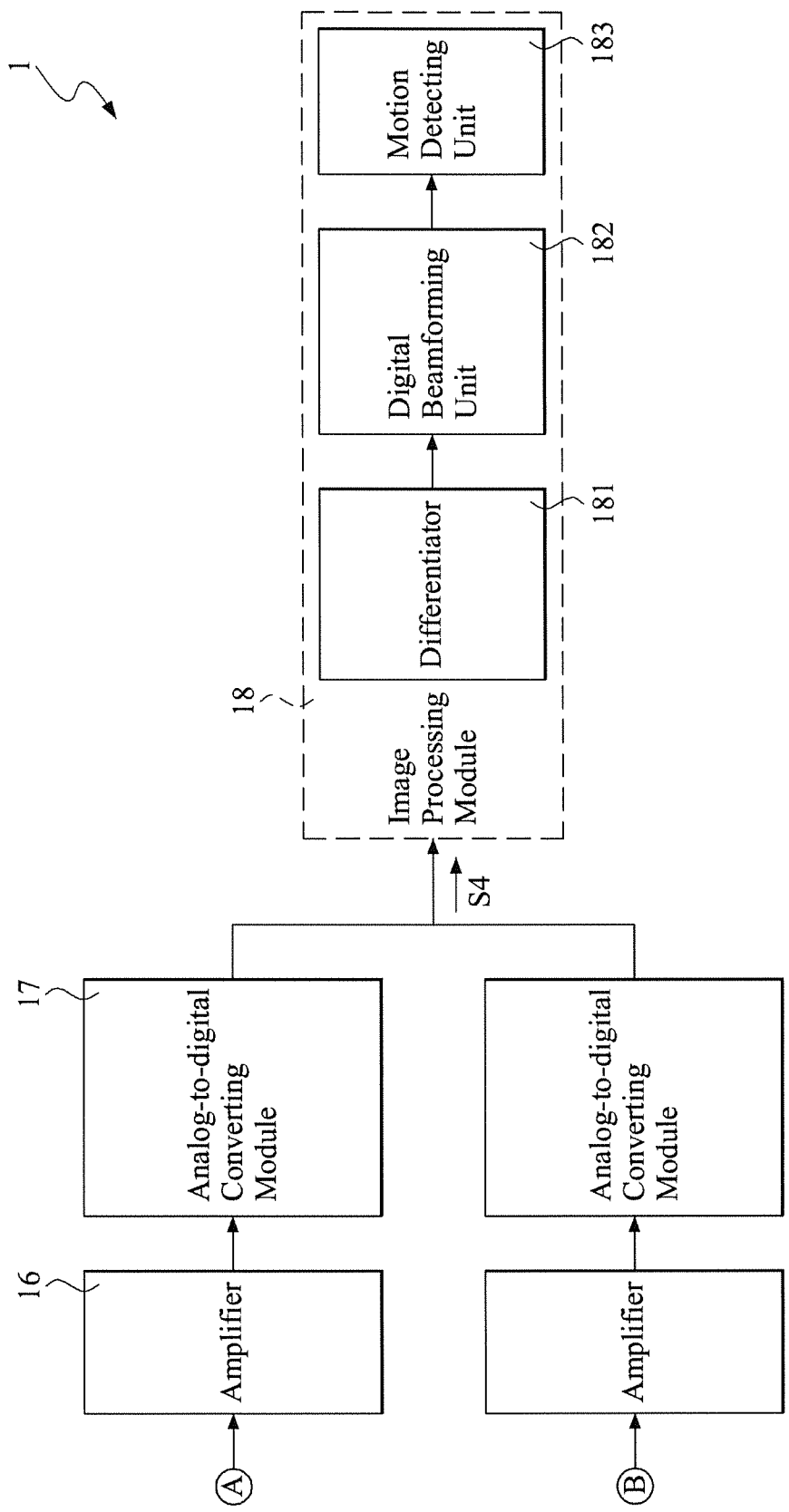

Refer to FIG. 1 and FIG. 1A, schematic views showing an ultrasonic imaging system according to an embodiment of the present invention. As it is shown in FIG. 1, an ultrasonic imaging system 1 generates an ultrasonic image of a motion status of an object (not shown) according to at least an ultrasonic motion signal S1 generated by detecting a motion of the object, the ultrasonic imaging system 1 including an ultrasonic probe 11, a plurality of demodulation modules 12 (only four are illustrated, and one is identified with referential number in the figure), a plurality of analog sub-array beamformers 13 (only two are illustrated, and one is identified with referential number in the figure), a plurality of integrators 14 (only two are illustrated, and one is identified with referential number in the figure), a plurality of filters 15 (only two are illustrated, and one is identified with referential number in the figure), a plurality of amplifiers 16 (only two are illustrated, and one is identified with referential number in the figure), a plurality of analog-to-digital converting modules 17 (only two are illustrated, and one is identified with referential number in the figure) and an image processing module 18. The object includes movable objects. According to a first embodiment of the present invention, the object is blood and the ultrasonic imaging system is for blood flow velocity estimation.

The ultrasonic probe 11 is selected from the group of probes forming one-dimensional array and probes forming two-dimensional array, but is not limited. The demodulation modules 12 electrically connect the ultrasonic probe 11 and include a demodulation circuit. The analog sub-array beamformers 13 electrically connect the demodulation modules 12. Further, the analog sub-array beamformers 13 includes a plurality of phase retarders 131 (only one is identified with referential number in the figure) and a plurality of adders 132 (only one is identified with referential number in the figure). The phase retarders 131 electrically connect demodulation modules 12 and the adders 132 electrically connect the phase retarders 131.

The integrators 14 electrically connect the analog sub-array beamformers 13 and electrically connect the adders 132; the filters 15 electrically connect the integrators 14 and are selected from the group of a high pass filter, a band pass filter and a low pass filter, but are not limited thereof. The amplifiers 16 electrically connect the filters 15; the analog-to-digital converting modules 17 electrically connect the amplifiers 16 and include an analog-to-digital converter (ADC).

The image processing module 18 electrically connects the analog-to-digital converting modules 17 and goes through at least a processing selected from the group of an image synthesis, an image analysis, an image calculation, an image data storage and a diagnosis assistance. According to an embodiment of the present invention, the image processing module 18 is coupled to the analog-to-digital converting modules 17 via a communication method selected from the group of radio frequency (RF), wireless fidelity (Wi-Fi) and Worldwide Interoperability for Microwave Access (WIMAX) and is not limited.

In addition, the image processing module 18 is selected from the group of hardware circuit, computer program software, communication device (such as a tablet or a laptop), and device with processing functionality. Furthermore, the image processing module 18 includes a differentiator 181, a digital beamforming unit 182 and a motion detecting unit 183. The digital forming unit 182 electrically connects the differentiator 181 and includes a beamformer; the motion detecting unit 183 electrically connects the digital beamforming unit 182 and includes a flow velocity detector.

Continue referring to FIG. 1 and FIG. 1A. The ultrasonic probe 11 generates the ultrasonic motion signal S1 by detecting the motion of the object (i.e., the above-mentioned flow velocity), wherein according to an embodiment of the present invention, the ultrasonic motion signal 51 includes an RF signal. The demodulation modules 12 receive and demodulate the ultrasonic motion signal S1 to generate and send a demodulated signal S2. The analog sub-array beamformers 13 receive the demodulated signal S2, generate and send an analog sub-array beam signal S3 according to the demodulated signal S2. Furthermore, the phase retarders 131 delay the phase of the demodulated signal S2 and the adders 132 sum the phase delayed demodulated signal S2 and generate the analog sub-array beam signal S3 accordingly (according to the first embodiment of the present invention, since there is only one phase retarder 131, the adder 132 merely sums a demodulation signal S2), wherein according to the first embodiment of the present invention, the analog sub-array beam signal S3 does not go through beamforming and therefore includes a sub-array beam signal.

The integrators 14 perform integration of the analog sub-array beam signal S3 (increasing the strength of DC signals). The filters 15 receive and filter the analog sub-array beam signal S3; more particularly, the filters 15 reject the DC signals and HF signals of the analog sub-array beam signal S3 and signals with flow velocity and special information are left. The amplifiers 16 further amplify the analog sub-array beam signal S3 filtered by the filters 15 and digitalize the sub-array beam signal S3 into a digital sub-array beam signal S4.

The image processing module 18 receives the digital sub-array beam signal S4 and generates the ultrasonic image of the motion of the object. Furthermore, the image processing module 18 includes the differentiator 181 to differentiate so as to return the digital sub-array beam signal S4. (Since the analog sub-array beam signal S3 is integrated by the integrators 14 before being digitalized and after the signal of the digital sub-array beam signal S4 is differentiated, it is still a digital sub-array beam signal; in other embodiments, the integrators 14 and the differentiator 181 are not required.) The digital beam forming unit 182 forms at least a digital beam and generates the ultrasonic image according to the digital sub-array beam signal S4. (Beamforming is prior art and is not to be mentioned here.) The motion detecting unit 183 detects the motion status of the object according to the ultrasonic image. Since according to the first embodiment of the present invention, the system detects the flow velocity, users learn the flow velocity and special information via the motion detecting unit 183. However, it is noted that the number of the ultrasonic motion signal S1, the demodulation signal S2, the analog sub-array beam signal S3 and digital sub-array beam signal S4 correspond to the number of the demodulation module 12, the analog sub-array beamformer 13, the integrator 14, the filter 15, the amplifier 16 and the analog-to-digital converting module 17.

It is worth mentioning that a multiple-gated calculation is utilized according to an embodiment of the present invention and the system includes multiple analog sub-array beamformers 13, and each analog sub-array beamformer 13 includes multiple phase retarders 131 (each corresponding to and electrically connecting to the demodulation module 12) and an adder 132. The phase retarders 131 perform phase delay and the adder 132 sums multiple demodulated signals S2 to form the analog sub-array beam signal S3. Further, according to an embodiment of the present invention, clutter filtering is performed on sub-array beam signals before digital beamforming, and signals received and sent continuously in each analog sub-array beamformer 13 are output timely via the filter 15. Thus, it is not needed to temporarily store the signals during imaging and thus the costs on scratchpad memory and computing of hardware are saved.

While the present invention has been particularly shown and described with reference to a preferred embodiment, it will be understood by those skilled in the art that various changes in form and detail may be without departing from the spirit and scope of the present invention.

What is claimed is:

1. An ultrasonic imaging system, for generating an ultrasonic image of a motion status of an object according to at least an ultrasonic motion signal generated by detecting a motion of the object, the ultrasonic imaging system comprising,
   at least a demodulation module receiving and demodulating the ultrasonic motion signal to generate and send at least a demodulated signal along a downstream signal direction;
   at least an analog sub-array beamformer electrically connecting the demodulation module, receiving the demodulated signal, and generating and sending an analog sub-array beam signal according to the demodulated signal;
   at least a filter electrically connecting the analog sub-array beamformer, and receiving and filtering the analog sub-array beam signal, the filter disposed downstream of the analog sub-array beamformer;
   at least an analog-to-digital converting module electrically connecting the filter and converting the analog sub-array beam signal filtered by the filter into a digital sub-array beam signal; and
   an image processing module receiving the digital sub-array beam signal, the image processing module including a digital beamforming unit disposed downstream of the analog sub-array beamformer and the filter, the image processing module forming a digital beam according to the digital sub-array beam signal to generate an ultrasonic image of the motion of the object.

2. The system according to claim 1, further comprising at least an ultrasonic probe electrically connecting the demodulation module, the ultrasonic probe detecting the motion of the object and generating the ultrasonic motion signal.

3. The system according to claim 1, wherein the analog sub-array beamformer includes at least a phase retarder and an adder, the phase retarder electrically connecting the demodulation module, and adder electrically connecting the phase retarder, the phase retarder delaying the phase of the demodulated signal, the adder summing the phase delayed demodulated signal and generating the analog sub-array beam signal accordingly.

4. The system according to claim 1, further comprising an integrator disposed between the analog sub-array beamformer and the filter, the integrator electrically connecting the analog sub-array beamformer and the filter to perform integration of the analog sub-array beam signal.

5. The system according to claim 1, wherein the image processing module includes a differentiator to differentiate the digital sub-array beam signal.

6. The system according to claim 1, wherein the image processing module further includes a motion detecting unit, the motion detecting unit electrically connecting the digital beamforming unit, the motion detecting unit detecting the motion status of the object according to the ultrasonic image.

7. The system according to claim 1, further comprising an amplifier disposed between the filter and the analog-to-digital converting module, the amplifier electrically connecting the filter and the analog-to-digital converting module to amplify the analog sub-array beam signal filtered by the filter.

8. The system according to claim 1, wherein the image processing module is coupled to the analog-to-digital converting module.

9. The system according to claim 1, wherein the image processing module goes through at least a processing selected from the group of an image synthesis, an image analysis, an image calculation, an image data storage and a diagnosis assistance.

10. The system according to claim 1, wherein the filter is selected from the group of a high pass filter, a band pass filter and a low pass filter.

* * * * *